United States Patent
Jin et al.

(10) Patent No.: US 7,632,877 B2
(45) Date of Patent: *Dec. 15, 2009

(54) DENTAL RESINS, DENTAL COMPOSITE MATERIALS, AND METHOD OF MANUFACTURE THEREOF

(75) Inventors: Shuhua Jin, Wallingford, CT (US); Weitao Jia, Wallingford, CT (US)

(73) Assignee: Pentron Clinical Technologies LLC, Wallingford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/696,872

(22) Filed: Apr. 5, 2007

(65) Prior Publication Data

US 2007/0173558 A1 Jul. 26, 2007

Related U.S. Application Data

(62) Division of application No. 10/452,269, filed on Jun. 2, 2003, now Pat. No. 7,241,856.

(51) Int. Cl.
*A61K 6/083* (2006.01)
*C08G 59/02* (2006.01)
*A61C 5/00* (2006.01)

(52) U.S. Cl. .............. 523/113; 523/116; 528/301; 433/228.1

(58) Field of Classification Search .............. 523/113; 528/301
See application file for complete search history.

(56) References Cited

U.S. PATENT DOCUMENTS

| | | | |
|---|---|---|---|
| 3,066,112 A | 11/1962 | Bowen | |
| 3,179,623 A | 4/1965 | Bowen | |
| 3,194,784 A | 7/1965 | Bowen | |
| 3,367,992 A | 2/1968 | Bearden | |
| 3,751,399 A | 8/1973 | Lee, Jr. et al | |
| 3,755,420 A | 8/1973 | Stoffey et al | |
| 3,926,906 A | 12/1975 | Lawrence et al | |
| 4,002,669 A * | 1/1977 | Gross et al. ................. | 560/126 |
| 4,306,913 A | 12/1981 | Mable et al. | |
| 4,544,359 A | 10/1985 | Waknine | |
| 4,547,531 A | 10/1985 | Waknine | |
| 4,764,497 A | 8/1988 | Yuasa et al. | |
| 5,276,068 A | 1/1994 | Waknine | |
| 5,444,104 A | 8/1995 | Waknine | |
| 5,484,867 A | 1/1996 | Lichtenhan et al. | |
| 5,830,951 A | 11/1998 | Fiedler | |
| 5,856,373 A | 1/1999 | Kaisaki et al. | |
| 5,876,210 A | 3/1999 | Klee et al. | |
| 5,936,006 A | 8/1999 | Rheinberger et al. | |
| 5,969,000 A | 10/1999 | Yang et al. | |
| 6,013,694 A | 1/2000 | Jia et al. | |
| 6,084,004 A | 7/2000 | Weinmann et al. | |
| 6,187,833 B1 | 2/2001 | Oxman et al. | |
| 6,187,836 B1 | 2/2001 | Oxman et al. | |
| 6,306,926 B1 | 10/2001 | Bretscher et al. | |
| 6,362,251 B1 | 3/2002 | Alkemper et al. | |
| 6,387,981 B1 | 5/2002 | Zhang et al. | |
| 6,417,246 B1 | 7/2002 | Jia et al. | |
| 6,572,693 B1 | 6/2003 | Wu et al. | |
| 6,653,365 B2 | 11/2003 | Jia | |
| 7,041,164 B2 * | 5/2006 | Kanca, III ..................... | 106/35 |
| 7,160,941 B2 | 1/2007 | Jin et al. | |
| 7,241,856 B2 | 7/2007 | Jin et al. | |
| 7,282,195 B2 * | 10/2007 | MacDougald et al. ......... | 424/49 |
| 7,470,728 B2 | 12/2008 | Jia et al. | |
| 2004/0235981 A1 * | 11/2004 | Qian .......................... | 523/115 |
| 2006/0009540 A1 | 1/2006 | Jia et al. | |
| 2008/0145820 A1 * | 6/2008 | Karmaker et al. ........... | 433/220 |

OTHER PUBLICATIONS

Feher, F.J. et al., "Silsequioxanes As Models For Silica Surfaces", J. Am. Chem. Soc. 1989, 111, 1741-1748.
Lichtenhan, J., "Polyhedral Oligomeric Silsesquioxanes: Building Blocks For Silsequioxane-Based Polymers And Hybrid Materials", Comments Inorg. Chem., 1995, vol. 17, No. 2, pp. 115-130.
Lichtenhan, J.D. et al, "Linear Hybrid Polymer Building Blocks: Methacrylate-Functionalized Polyhedral Oligomeric Silsesquioxane Monomers And Polymers", Macromolecules 1995, 28, 8435-8437.
"High Performance POSS-Modified Polymeric Composites", NASA Tech Briefs, Feb. 2001 issue p. 52.
JP 82004646; Publication Date: Jan. 27, 1982 (translation of abstract only).
S57-004646; Jan. 27, 1982; Translation; 7 pages.

* cited by examiner

*Primary Examiner*—Tae H Yoon
(74) *Attorney, Agent, or Firm*—Cantor Colburn LLP

(57) ABSTRACT

A low shrinkage, polymerizable oligomer comprises units of the structure:

$$AB \qquad (I)$$

wherein A is an organic radical comprising 1 to about 6 (meth)acrylate groups and 0 to about 5 hydroxy groups; B is an organic radical comprising 1 to about 5 epoxide groups, and wherein A and B are linked through the reaction of an epoxide and a hydroxy group. In one embodiment, a dental restorative material comprises the low shrinkage, polymerizable dental oligomer, a filler system, and a curing system. These polymerizable dental resins may be used for a variety of dental materials, treatments, and restorative functions, including crown and bridge materials, fillings, adhesives, sealants, luting agents or cements, denture base materials, orthodontic materials and sealants, and other dental restorative materials.

9 Claims, No Drawings

DENTAL RESINS, DENTAL COMPOSITE MATERIALS, AND METHOD OF MANUFACTURE THEREOF

CROSS-REFERENCE TO RELATED APPLICATIONS

This application is a division of U.S. application Ser. No. 10/452,269 filed Jun. 2, 2003, now U.S. Pat. No. 7,241,856, which is fully incorporated herein by reference.

BACKGROUND

This invention relates to polymerizable dental resins for dental composite materials and the method of manufacture of such resins for restorative dentistry, and more particularly to dental composite materials that are useful as crown and bridge materials either with or without an alloy substrate, as reconstructive materials, restorative materials, filling materials, inlays, onlays, laminate veneers, dental adhesives, cements, sealants and the like.

In recent years, materials used for dental restorations have comprised principally of acrylate or methacrylate resins. Typical acrylic resinous materials are disclosed, for example, in U.S. Pat. No. 3,066,112 to Bowen, U.S. Pat. No. 3,194,784 to Bowen, and U.S. Pat. No. 3,926,906 to Lee et al. An especially important methacrylate monomer is the condensation product of bisphenol A and glycidyl methacrylate, 2,2'-bis[4-(3-methacryloxy-2-hydroxy propoxy)-phenyl]-propane (Bis-GMA). Alternatively, BisGMA may be synthesized from the diglycidyl ether of bisphenol A and methacrylic acid (see U.S. Pat. No. 3,066,112 to Bowen).

Because the wear and abrasion characteristics and the overall physical, mechanical, and optical properties of these unfilled acrylic resinous materials is poor, and because acrylic resin systems exhibit high coefficients of thermal expansion relative to the coefficient of thermal expansion of the tooth structure, these substances by themselves are less than satisfactory. In particular, the disparity in thermal expansion coupled with high shrinkage upon polymerization results in poor marginal adaptability, and ultimately leads to secondary decay. Composite acrylic dental restorative materials containing acrylate or methacrylate resins and fillers were thus developed, the fillers generally comprise inorganic materials based on silica, silicate based glasses, or quartz. These filled compositions are useful for a variety of dental treatments and restorative functions including crown and bridge materials, fillings, adhesives, sealants, luting agents or cements, denture base materials, orthodontic materials and sealants, and other dental restorative materials. Despite their suitability for their intended purposes, however, many of these materials have shrinkages of about two to about 4% by volume upon polymerization.

Alternative resinous materials include the ring-opening polymerization of epoxides. These resins have lower shrinkage than methacrylates, but exhibit compatibility problems with methacrylate bonding adhesives and cements when used together.

Epoxy/(meth)acrylate containing compounds containing both epoxy and (meth)acrylate functionality are also known and are obtained from reaction of multi-epoxide containing compound with one or less equivalent of (meth)acrylic acid, or reaction of hydroxyl containing (meth)acrylate with epichlorohydrin. Commercially available epoxy/methacrylate include 3,4-epoxy-cyclohexyl methyl methacrylate from Daicel Chemical, Japan. U.S. Pat. No. 6,187,833 to Oxman et al. generally discloses photocurable compositions containing an epoxy resin, a hydroxyl-containing material, and optionally a free radically polymerizable material. The compositions contain a ternary photoinitiator system comprising an iodonium salt, a visible light sensitizer, and an electron donor compound. Oxman et al. disclose a bifunctional epoxy/acrylate material, but do not disclose an epoxy/acrylate oligomeric material made from the reaction product of a multi-epoxide containing compound and hydroxy(meth)acrylate.

There remains a need in the art for dental resin materials that have minimal shrinkage without sacrificing other advantageous physical properties. It is further desirable to improve other properties of the cured material such as fracture toughness.

SUMMARY

A polymerizable dental resin having low shrinkage upon polymerization comprises the polymerization product of an oligomer comprising a (meth)acrylate functionality and an epoxy functionality. In a preferred embodiment, the oligomer comprises units of the general structure (I):

$$AB \qquad (I)$$

wherein A is an organic radical comprising 1 to about 6 (meth)acrylate groups and 0 to about 5 hydroxy groups; and B is an organic radical comprising 1 to about 5 epoxide groups, and A and B are linked through the reaction of an epoxide and a hydroxy group. The polymerizable dental oligomer is conveniently synthesized by the selective reaction of a multifunctional epoxide with a hydroxy(meth)acrylate to yield a reactive, polymerizable dental oligomer having an epoxy functionality and an ethylenically unsaturated functionality.

In another embodiment, the polymerizable dental resin comprises the reaction product of a hydroxy(meth)acrylate of the formula

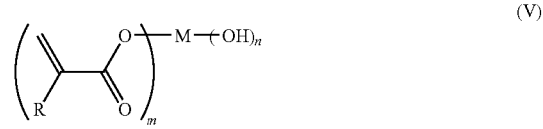

(V)

wherein m and n are independently integers of 1 to about 6; M is a substituted or unsubstituted $C_1$ to $C_{33}$ alkyl or aryl group; and R is hydrogen or methyl; and a multifunctional epoxide of the formula

(II)

wherein E is a substituted or unsubstituted allyl, alkoxy, alkylether, heterocycle, alkaryl, or aryl group, and x is an integer of 2 to about 6.

In yet another embodiment is a method of manufacturing a polymerizable dental resin comprising reacting, in the presence of a curing system, the above-described hydroxy(meth)acrylate; and multifunctional epoxide.

In another embodiment, a dental restorative material comprises the low shrinkage, polymerizable dental resin comprising oligomer of structure (I), an optional filler system, and a curing system. In the formulation of dental restorative materials, both the epoxide functionality and the (meth)acrylate functionality can participate in the polymerization. These two functionalities can be activated simultaneously or one functionality may be activated selectively. The curing system can be a self-cure or a photocure system. The polymerizable dental resins may be used for a variety of dental materials, treatments, and restorative functions, including crown and bridge materials, fillings, adhesives, sealants, luting agents or cements, denture base materials, orthodontic materials and sealants, and other dental restorative materials.

DETAILED DESCRIPTION OF PREFERRED EMBODIMENTS

It has unexpectedly been discovered that a polymerizable dental resin oligomer having both an epoxy functionality and a (meth)acrylate functionality has improved low shrinkage upon curing, together with improved fracture resistance. Furthermore, it has been discovered that the use of a cationic initiator in the polymerization of the dental resin is not necessary, although it may optionally be used. As used herein, the term "(meth)acrylate" is intended to encompass both acrylate and methacrylate groups. The term "multifunctional epoxide" is intended to encompass an organic compound comprising at least two epoxide functionalities. The term "hydroxy(meth)acrylate" is intended to encompass an organic compound comprising at least one hydroxy functionality and at least one (meth)acrylate functionality.

In particular, an unexpectedly improved polymerizable oligomer comprises units of structure (I)

AB  (I)

wherein A is an organic radical comprising 1 to about 6 (meth)acrylate groups and 0 to about 5 hydroxy groups; and B is an organic radical comprising 1 to about 5 epoxide groups, wherein A and B are linked through the reaction of an epoxide and a hydroxy group. The general structure of (I) can have a variety of forms, for example A and B call be in alternating order (e.g., ABAB . . . ) and/or branched. In one embodiment, the oligomer has the form $A_aB_b$ wherein a is an integer from 2 to 10, b is one, A is a monovalent radical, and B is a radical having a valency corresponding to a. In another embodiment, a is 1, b is an integer from 2 to 10, A is a radical having a valency corresponding to b, and B is a monovalent radical.

The oligomer (I) is synthesized from the reaction of a multifunctional epoxide and a hydroxy(meth)acrylate in the presence of a catalyst and heat. Preferably the amount of hydroxy groups in the hydroxy(meth)acrylate is less than one equivalent per equivalent of epoxide. Depending upon the reaction conditions, such as ratio of hydroxy to epoxy, the reaction temperature and time, and the amount of catalyst, the reaction product may comprise a variety of one or more compounds, including the unreacted epoxides and hydroxy (meth)acrylates, the oligomer of structure (I), and a polymeric epoxy/(meth)acrylate or polyepoxides resulting from the ring-opening of the epoxides.

Suitable multifunctional epoxides are compounds having two or more epoxide (oxirane) functionalities, and include monomeric epoxy compounds and epoxides of the oligomeric or polymeric type, which can be aliphatic, cycloaliphatic, aromatic, or heterocyclic. These multifunctional epoxides may vary from low molecular weight monomeric materials to oligomers to high molecular weight polymers and may vary greatly in the nature of their backbone and substituent groups, provided that the backbone and the substituents thereon can be molecular groups that do not substantially interfere with the cure of the polymerizable dental resin at room temperature. Illustrative of permissible substituent groups include halogens, ester groups, ethers, sulfonate groups, siloxane groups, nitro groups, phosphate groups, and the like.

The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl(meth)acrylate polymer or copolymer). These epoxides generally have, on average, greater than or equal to about two polymerizable epoxy groups per molecule. The "average" number of epoxy groups per molecule is determined by dividing the total number of epoxy groups in the multifunctional epoxide by the total number of epoxy-containing molecules present.

The epoxides may be pure compounds or may be mixtures of compounds having greater than or equal to about two polymerizable epoxy groups per molecule. The number average molecular weight ($M_n$) of the epoxy-containing materials is about 58 to about 20,000 g/mole. Examples of mixtures include two or more multifunctional epoxides having different number average molecular weight distributions of epoxy-containing compounds, such as a low molecular weight (below 200 g/mole) blended with an intermediate molecular weight (about 200 to about 1,000 g/mole) and/or higher molecular weight (above about 20,000 g/mole). Alternatively or additionally, the multifunctional epoxide may comprise a blend of multifunctional epoxides having different chemical natures, such as aliphatic and aromatic, or functionalities, such as polar and non-polar.

Useful multifunctional epoxides include those that contain cyclohexene oxide groups such as epoxycyclohexanecarboxylates, typified by 3,4-epoxycyclohexylmethyl-3,4-epoxycyclohexanecarboxylate; 3,4-epoxy-2-methylcyclohexylmethyl-3,4-epoxy-2-methylcyclohexane carboxylate; and bis(3,4-epoxy-6-methylcyclohexylmethyl)adipate.

Other multifunctional epoxides that are of particular utility in forming the polymerizable dental resins include the formula (II)

(II)

wherein E is a substituted or unsubstituted alkyl, alkoxy, alkylether, heterocycle, alkaryl, or aryl group and x is an integer of 2 to about 6. Suitable substitutions on the E moiety include, but are not limited to, linear or branched, saturated or unsaturated $C_1$-$C_{12}$ alkyl; cyclic $C_3$-$C_7$ alkyl; halogens; ester groups; ether groups; amide groups; aryl; and the like.

In particular, the multifunctional epoxide may have the formula (III):

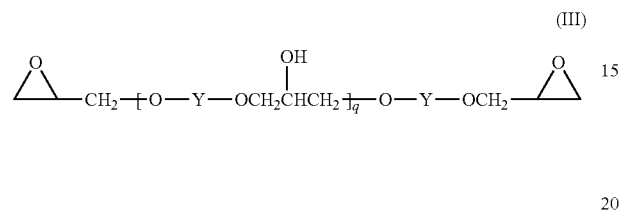

(III)

wherein Y is a divalent $C_1$-$C_{33}$ substituted or unsubstituted alkyl, alkoxy, aryl, alkylether, heterocycle, or alkaryl group, and q is 0 to about 20. Preferably, Y is a divalent $C_6$-$C_{18}$ aryl or $C_1$-$C_{33}$ alkyl or alkylether-containing group, and q is an integer of 0 to about 10. Suitable substitution on the Y moiety include, but is not limited to, linear or branched, saturated or unsaturated $C_1$-$C_{12}$ alkyl; cyclic $C_3$-$C_7$ alkyl; halogens; ester groups; ether groups; amide groups; aryl; and the like.

A particularly preferred multifunctional epoxide is an aromatic diglycidyl ether having the formula (IV):

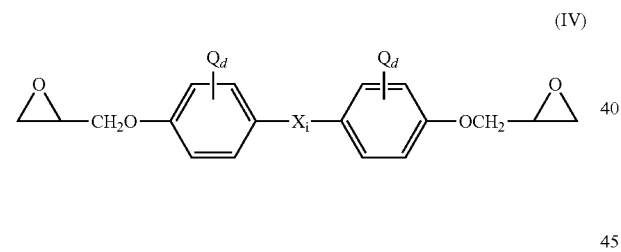

(IV)

wherein X is oxygen, sulfur, carbonyl, or a divalent $C_1$-$C_6$ alkyl, alkylether, or aryl group, d is an integer of 1 to 4, and i is an integer of 0 to about 6. Preferably, X is a divalent alkyl or alkylether-containing group. Q is hydrogen or halogen, such as chlorine, bromine and iodine; and d is an integer of 2, 3, or 4. Preferably Q is hydrogen or bromine.

Further examples of suitable multifunctional glycidyl ethers are the glycidyl ethers of polyhydric phenols obtained by reacting a polyhydric phenol with an excess of a chlorohydrin such as epichlorohydrin, e.g., the diglycidyl ether of 2,2-bis-(2,3-epoxypropoxyphenol)-propane (Bisphenol A); brominated diglycidyl ether of bisphenol A, the diglycidyl ether of Bisphenol F; the 1,4-butanediol diglycidyl ether of phenolformaldehyde novolak (e.g., "DEN-431" and "DEN-438" from Dow Chemical Company); resorcinol diglycidyl ether (e.g., "KOPOXITE" from Koppers Company, Inc.); and polyfunctional glycidyl ethers such as the diglycidyl ether of 1,4-butanediol, the diglycidyl ether of neopentyl glycol, the diglycidyl ether of cyclohexanedimethanol, trimethylol ethane triglycidyl ether, trimethylol propane triglycidyl ether, and mixtures comprising at least one of the foregoing ethers.

The hydroxy(meth)acrylate compounds used to synthesize the oligomer of the may contain a hydroxyl group terminally situated or pendent from a polymeric or copolymeric(meth)acrylate. A general structure of the hydroxy(meth)acrylate is shown in formula (V):

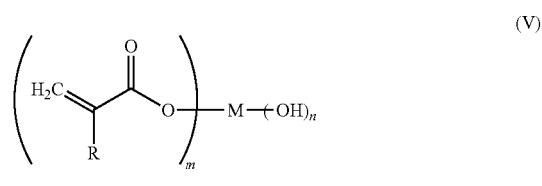

(V)

wherein m and n are independently integers from 1 to 6; M is a substituted or unsubstituted $C_1$-$C_{33}$ alkyl or aryl group; and R is hydrogen or methyl. Suitable substitution on the M moiety include, but is not limited to, linear or branched, saturated or unsaturated $C_1$-$C_{12}$ alkyl; cyclic $C_3$-$C_7$ alkyl; halogens; ester groups; ether groups; amide groups; aryl; and the like.

A preferred hydroxy(meth)acrylate is a linear monofunctional hydroxy(meth)acrylate wherein m and n equal 1, as shown in formula (VI):

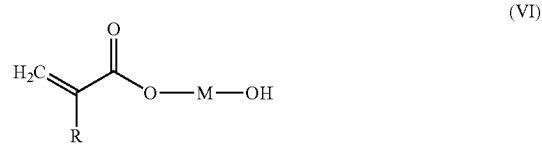

(VI)

Non-limiting examples of suitable hydroxy(meth)acrylates include caprolactone 2-(methacryloyloxy) ethyl ester (CLMA); 2-hydroxyethyl acrylate; 2-hydroxyethyl methacrylate (HEMA); 3-hydroxypropyl(meth)acrylate; 4-hydroxybutyl(meth)acrylate; polyethylene glycol mono(meth)acrylate; glycerol di(meth)acrylate; trimethylolpropane di(meth)acrylate; pentaerythritol tri(meth)acrylate; and the (meth)acrylate of phenyl glycidyl ether. Blends of the aforementioned hydroxy(meth)acrylates can also be used to form the polymerizable dental resin. The most preferred hydroxy acrylate or hydroxy methacrylate is CLMA and HEMA.

In one preferred embodiment, reaction of multifunctional epoxy (IV) with monofunctional hydroxy(meth)acrylate (VI) yields a reaction product comprising a mixture of products, including a polymerizable oligomer having the structure (VII):

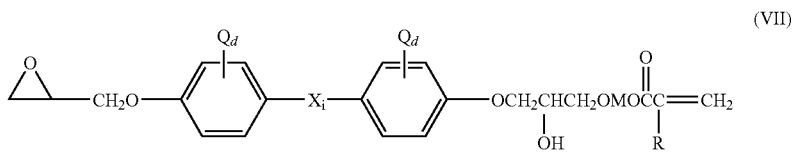

wherein X, M, R, Q, d, and i are as defined above.

Further non-limiting examples of preferred polymerizable oligomers include the structures (VIII) and (IX):

or iodine; q is 0 to about 20; M is a substituted or unsubstituted $C_1$-$C_{33}$ alkyl or aryl group; R is hydrogen or methyl; and d is 2, 3, or 4.

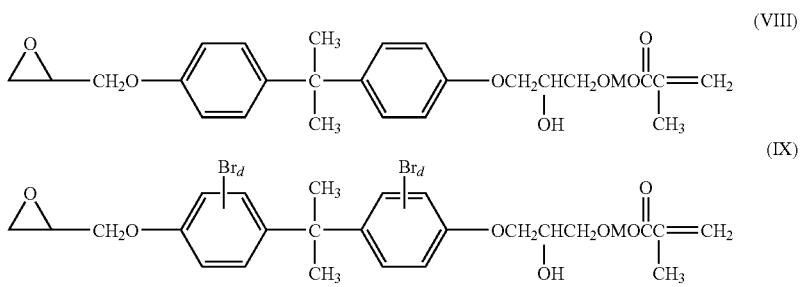

wherein M is a divalent linear $C_2$-$C_4$ alkyl group, a divalent linear $C_1$-$C_{10}$ alkoxy group, e.g., $(-OCH_2CH_2-)_{1-10}$, or a $C_2$-$C_{10}$ divalent linear ester group, e.g., $-(CH_2)_4C(O)OCH_2CH_2$.

In still another embodiment, the oligomer has the structure (X):

In the formation of the oligomers, the amount of hydroxy (meth)acrylate is selected so as to result in the polymerizable resin having a molar ratio of epoxy:(meth)acrylate groups of about 1:10 to about 10:1, preferably about 1:5 to about 5:1, more preferably about 2:1 to about 1:2. Suitable amounts may be readily selected by one of ordinary skill in the art, depend-

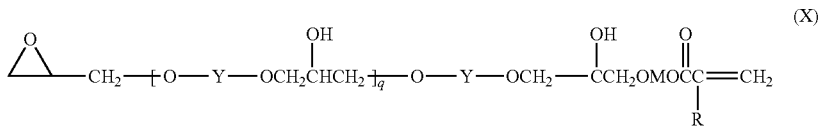

wherein Y is a divalent $C_1$ to $C_{33}$ substituted or unsubstituted alkyl, alkoxy, aryl, alkylether, heterocyclic, or alkaryl group; M is a substituted or unsubstituted $C_1$-$C_{33}$ alkyl or aryl group; R is hydrogen or methyl; and q is 0 to about 20.

In yet another embodiment, the oligomer has the structure (XI)):

ing on the reactivity of the epoxide and hydroxy(meth)acrylate compounds, reaction conditions, and the like. Suitable reaction conditions are known to those of skill in the art.

The catalyst can be selected from those used in conventional cationic, anionic or coordination ring-opening polymerization. Preferred catalysts are metal organic catalysts

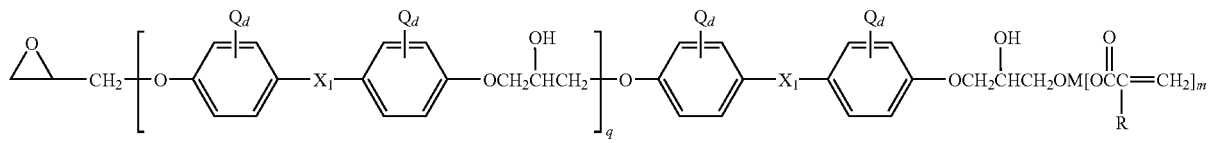

wherein m is 1 to 3, preferably 1; X is oxygen, sulfur, carbonyl, or a divalent substituted or unsubstituted $C_1$-$C_6$ alkyl or aryl group; i is 0 to about 6; Q is hydrogen, chlorine, bromine comprising tin or titanium. Suitable non-limiting examples of tin-containing catalysts are dibutyltin dilaurate, dibutyltin maleate, dibutyltin diacetate, dioctyltin maleate, dibutyltin phthalate, stannous octoate, stannous naphthenate, stannous stearate, stannous 2-ethyl hexanoate, dibutyltin diacetylacetonate, dibutyltin oxide, and combinations comprising at least one of the foregoing tin based catalysts. Suitable non-limiting examples of titanium-based catalysts are tetrabutyl titanate, tetrapropyl titanate, tetraisopropyl titanate, triethanolamine titanate, titanium tetraacetylacetonate, and combinations comprising at least one of the foregoing titanium based catalysts. The preferred catalysts are stannous octoate or stannous 2-ethyl hexanoate.

It is generally desirable to use the catalyst in an amount of about 0.10 to about 10 mole percent (mole %) based on the total moles of the reactant mixture. Within this range it is generally desirable to utilize the catalyst in an amount of greater than or equal to about one, preferably greater than or equal to about 2, and most preferably greater than or equal to about 3 mole % based on the total moles of the reactants. Within this range, it is generally desirable to utilize the catalyst in an amount of less than or equal to about 8, and preferably less than or equal to about 7 mole % based on the total moles of the reactants.

The above-described polymerizable dental resin can be used together with a curing system, other optional viscous resins, optional diluents, and/or an optional filler system to provide a dental restorative material for the formation of dental restorations. It is generally desirable to use the above-described polymerizable dental resin in an amount of about 1 to about 99 weight percent (wt %) based on the total weight of the dental restorative material. Within this range it is generally desirable to use the polymerizable dental resin in an amount of greater than or equal to about 10, preferably greater than or equal to about 30, and most preferably greater than or equal to about 50 wt % based on the total weight of the dental restorative material. Within this range, it is generally desirable to utilize the polymerizable dental resin in an amount of less than or equal to about 95, and preferably less than or equal to about 90 wt % based on the total weight of the dental restorative material.

Known viscous resins may be added to the polymerizable dental resin to provide a dental restorative material. Non-limiting examples include polyurethane dimethacrylates (PUDMA), diurethane dimethacrylates (DUDMA), and/or the polycarbonate dimethacrylate (PCDMA) disclosed in U.S. Pat. Nos. 5,276,068 and 5,444,104 to Waknine, which is the condensation product of two parts of a hydroxyalkyl-methacrylate and 1 part of a bis(chloroformate). Another advantageous resin having lower water sorption characteristics is an ethoxylated bisphenol A dimethacrylate (EBP-DMA) as disclosed in U.S. Pat. No. 6,013,694. An especially useful methacrylate resin is the condensation product of bisphenol A and glycidyl methacrylate, 2,2'-bis[4-(3-methacryloxy-2-hydroxy propoxy)-phenyl]-propane (Bis-GMA).

Diluent monomers may be used to increase the surface wettability of the composition and/or to decrease the viscosity of the polymerization medium. Suitable diluent monomers include those known in the art such as hydroxy alkyl methacrylates, for example 2-hydroxyethyl methacrylate and 2-hydroxypropyl methacrylate; ethylene glycol methacrylates, including ethylene glycol methacrylate, diethylene glycol methacrylate, tri(ethylene glycol)dimethacrylate and tetra (ethylene glycol)dimethacrylate; and diol dimethacrylates such as butanedimethacrylate, dodecanedimethacrylate, or 1,6-hexanedioldimethacrylate (HDDMA). Tri(ethylene glycol)dimethacrylate (TEGDMA) is particularly preferred.

Diluent monomers or viscous resins, when present, are incorporated into the dental restorative materials in an amount of about 1 to about 70 wt % of the total dental restorative material.

The optional filler composition may comprise one or more of the inorganic fillers currently used in dental composite materials. Preferred fillers include those, which are capable of being covalently bonded to the low shrinkage, polymerizable dental resin matrix itself or to a coupling agent (e.g., silanes) that is covalently bonded to both. Examples of suitable filling materials include but are not limited to, silica, quartz, strontium silicate, strontium borosilicate, lithium silicate, lithium alumina silicate, amorphous silica, ammoniated or deammoniated calcium phosphate, tricalcium phosphate alumina, zirconia, tin oxide, titania and combinations comprising at least one of the foregoing fillers. Some of the aforementioned inorganic filling materials and methods of preparation thereof are disclosed in U.S. Pat. Nos. 4,544,359 and 4,547,531, pertinent portions of which are incorporated herein by reference. Organic-inorganic fillers of POSS™ (Hybrid Plastics) can be incorporated into the composites as disclosed in co-assigned U.S. patent application Ser. No. 10/136,031. Other organic-inorganic fillers such as zirconium methacrylate and zirconium dimethacrylate under the codes of CXZR050 and CXZR051 (Gelest, Inc.) can also be used. Suitable high refractive index filler materials such as high refractive index silica glass fillers; calcium silicate based fillers such as apatites, hydroxyapatites or modified hydroxyapatite compositions may also be used. Alternatively, inert, non-toxic radiopaque materials such as bismuth oxide ($Bi_2O_3$), zirconium oxide, barium sulfate, and bismuth subcarbonate in micro- or nano scaled sizes may be used.

Suitable fillers have particle sizes of about 0.01 to about 5.0 micrometers, and may further comprise bound or unbound silicate colloids of about 0.001 to about 0.2 micrometers. These additional fillers may also be treated with a silane-coupling agent to increase adhesion with the low shrinkage, polymerizable dental resin. Commercially available silane treated fumed silica based on Aerosil A200 can be obtained from Degussa Corp under the names of Aerosil R711 and R7200.

The amount of total filler composition in the dental restorative material can vary from about 1 to about 90 wt % based on the total weight of the dental restorative material. The amount used is determined by the requirements of the particular application. Thus, for example, crown and bridge materials generally comprise about 60 to about 90 wt % filler; luting cements comprise about 20 to about 80 wt % filler; sealants generally comprise about 1 to about 20 wt % filler; adhesives generally comprise about 1 to about 30 wt % filler; and restorative materials comprise about 50 to about 90 wt % filler, with the remainder in all cases being the polymerizable dental resin and other optionally added resins.

The low shrinkage, polymerizable dental resin may be used together with a curing system, which generally includes polymerization initiators; polymerization accelerators; ultraviolet light absorbers; antioxidants; and other additives known in the art.

Suitable polymerization initiators are those initiators, which can be utilized in UV-activated cure or visible light-activated cure compositions. For example, visible light curable compositions employ light-sensitive compounds, including but not being limited to benzil, benzoin, benzoin methyl ether, DL-camphorquinone (CQ), and benzil diketones. Either UV-activated cure or visible light-activated cure (approximately 230 to 750 nm) is acceptable. The amount of photoinitiator is selected according to the curing rate desired.

A minimal catalytically effective amount is generally about 0.01 wt % of the total resin compositions, and will lead to a slower cure. Faster rates of cure are achieved with amounts of catalyst in the range from greater than about 0.01 percent to about 5 wt % of the dental composite material. The total resin composition is hereby defined as the total weight of the polymerizable dental resin and other resinous materials, such as for example, resinous diluents, which are used in the dental restorative material.

Alternatively, the dental restorative material may be formulated as a self-curing system. Self-curing dental composite materials will generally contain free radical polymerization initiators such as, for example, a peroxide in an amount of about 0.01 to about 1.0 wt % of the total resin dental composite material. Particularly suitable free radical initiators are lauryl peroxide, tributyl hydroperoxide and, more particularly benzoyl peroxide.

Polymerization accelerators suitable for use are the various organic tertiary amines well known in the art. In visible light curable dental composite materials, the tertiary amines are generally acrylate derivatives such as dimethylaminoethyl methacrylate and, particularly, diethylaminoethyl methacrylate (DEAEMA) in an amount of about 0.05 to about 0.5 wt % of the total dental composite material. In the self-curing dental composite materials, the tertiary amines are generally aromatic tertiary amines, preferably tertiary aromatic amines such as ethyl 4-(dimethylamino)benzoate (EDMAB), 2-[4-(dimethylamino)phenyl]ethanol, N,N-dimethyl-p-toluidine (DMPT), and bis(hydroxyethyl)-p-toluidine. Such accelerators are generally present in an amount of about 0.5 to about 4.0 wt % of the total dental composite material.

It is furthermore preferred to employ an ultraviolet absorber in an amount of about 0.05 to about 5.0 wt % of the total dental restorative material. Such UV absorbers are particularly desirable in the visible light curable dental restorative materials in order to avoid discoloration of the resin from incident ultraviolet light. Suitable UV absorbers are the various benzophenones, particularly UV-5411 available from American Cyanamid Company.

In a preferred embodiment, in one manner of proceeding, the polymerizable dental resin is prepared by reacting the multifunctional epoxide with the hydroxy acrylate and/or hydroxy methacrylate in the presence of a catalyst. The resulting polymerizable dental resin is then formulated into a dental restorative material by mixing with the filler composition and the curing system and applying to the tooth to be repaired.

Alternatively, the dental restorative material may be formulated as a two-part system, wherein the first part can comprise the low shrinkage, polymerizable dental resin, and the filler composition. The second part can comprise the curing system and optional diluent monomers. When necessary, the two parts are metered out and then mixed using a spatula. The cure may be initiated through the use of UV light or by raising the temperature of the mixture. The dental restorative material thus obtained is then placed in the tooth to be repaired after it is appropriately prepared. Methods for use of the above-described compositions are well known in the art.

The invention is further illustrated by the following non-limiting examples.

EXAMPLE 1

Samples of a bisphenol A monomer comprising an epoxy and a methacrylate group (bisphenol A epoxy/methacrylate, "BAEM") (Samples 1-3) or bisphenol F epoxy/methacrylate (BFEM) (Samples 4-6) were prepared by reacting either the diglycidyl ether of bisphenol A (DGEBA) or the diglycidyl ether of bisphenol F (DGEBF) with 2-hydroxyethyl methacrylate (HEMA), all obtained from Sigma-Aldrich, in the molar ratios of HEMA with epoxy shown in Table 1.

The mixture was stirred using a magnetic stirrer. The flask was maintained in an oil bath at a temperature of 130-170° C. during the course of the reaction. The reaction was catalyzed by the addition of 5 mole % (based on the total moles of the reactants) of stannous 2-ethylhexanoate (SEH) also obtained from Sigma-Aldrich. The total time of the reaction was from 2 to 8 hours. The reaction was monitored by FTIR and stopped when the intensity of C—O stretching in oxirane ring at 910 cm$^{-1}$ did not decrease significantly.

TABLE 1

| Sample No. | mole % of HEMA to epoxy | BAEM or BFEM |
| --- | --- | --- |
| 1 | 0.25 | BAEM1 |
| 2 | 0.50 | BAEM2 |
| 3 | 0.75 | BAEM3 |
| 4 | 0.25 | BFEM1 |
| 5 | 0.50 | BFEM2 |
| 6 | 0.75 | BFEM3 |

EXAMPLE 2

All the resin or resin combinations shown in Table 2 below were mixed with 3 wt % diaryliodonium hexafluoro antimonite commercially available from Sartomer Company, 0.3 wt % camphorquinone (CQ) obtained from Aldrich Chemicals Company and 0.2 wt % ethyl 4-(dimethylamino)benzoate (EDMAB) commercially available from Aldrich. Sample 11 is a comparative example and represents a blend of 70 wt % epoxy resin (DGEBA) with 30 wt % of an acrylate resin i.e., ethoxylated bisphenol A dimethacrylate (EBPADMA), while samples 12 and 13 represent a blend of the polymerizable dental resin of this disclosure i.e., 70 wt % BAEM1 or BAEM2 resin with 30 wt % EBPADMA, wherein the wt % is calculated with respect to the total weights of the respective BAEM resin and EBPADMA.

A small amount of the resin of each sample (0.2 grains) was placed in a mixing well and was cured using a visible light source Cure-Lite™ (commercially available from Pentron Corp.) for different time periods. Gel time is the time taken by the resin to reach an infinite viscosity and was determined using a spatula in the mixing well. Hardening time is the time taken by the resin to attain a hardened mass felt by touching with a spatula.

TABLE 2

| Sample No. | Composition | Gel Time | Hardening Time |
| --- | --- | --- | --- |
| 7 | DGEBA | 1 minute | 2 minutes |
| 8 | DGEBF | 6 minutes | 12 minutes |
| 9 | BAEM1 | 1 second | 5 minutes |
| 10 | BAEM2 | 1 second | 2 minutes |
| 11 | DGEBA/EBPADMA (70/30 wt. ratio) | 1 second | 4 minutes |
| 12 | BAEM1/EBPADMA (70/30 wt. ratio) | 1 second | 30 seconds |
| 13 | BAEM2/EBPADMA (70/30 wt. ratio) | 1 second | 12 seconds |
| 14 | EBPADMA | 1 second | 12 seconds |

As can be seen in Table 2, samples 9 and 10 obtained by the reaction of DGEBA with HEMA reach the gel point much more rapidly than the samples 7 and 8 obtained by reacting the epoxy precursors DGEBA and DGEBF respectively. Sample 11, which represents a blend of an epoxy resin with an acrylate resin gels within 1 second as do samples 12 and 13, which are blends of the polymerizable dental resin of this disclosure with EBPADMA. However, both samples 12 and 13 takes a much shorter time (approximately 30 seconds or less) to reach a hardened mass as compared with sample 11, which takes approximately 4 minutes. Thus blends comprising the polymerizable dental resin can generally be cured in a much shorter time period than the corresponding comparative blend.

EXAMPLE 3

Samples 15-17 were made by mixing BAEM1 with EBPADMA in different weight ratios as indicated in Table 3. These samples were cured by utilizing a curing system comprising 3% wt % diaryliodonium hexafluoro antimonite (SarCat®CD 1012, Sartomer Corp.), 0.3 wt % camphorquinone (CQ) and 0.2 wt % EDMAB where the percentages are calculated with respect to the total weight of the composition. Three point bending strength or flexural strength was measured on all samples using an ATS machine as per ISO 4049 for Resin Based Filling Materials (1997). The samples were cured for a total four minutes using visible light with CureLite™ Plus curing box (Pentron Corp.) Samples were then trimmed and stored in water at 37° C. for 24 hours before testing. The results are listed in Table 3.

TABLE 3

| Sample No. | Resin or resin combinations | Flexural strength in psi (standard deviation) |
|---|---|---|
| 15 | BAEM1/EBPADMA (70/30 wt ratio) | 18985 (941) |
| 16 | BAEM1/EBPADMA (50/50 wt ratio) | 18182 (1383) |
| 17 | BAEM1/EBPADMA (30/70 wt ratio) | 18631 (1128) |
| 18 | EBPADMA | 4571 (739) |

Table 3 clearly shows that the blends containing the BAEM and EBPADMA have superior flexural strength than those samples obtained by curing the EBPADMA alone.

The low shrinkage, polymerizable dental resin or blends comprising the polymerizable dental resin thus display a number of advantages over other resins used in dental composite materials. These resins or the blends comprising these resins generally display a shrinkage of less than or equal to about 8, preferably less than or equal to about 6, more preferably less than or equal to about 4, and most preferably less than or equal to about 2 volume percent upon curing as compared with the volume occupied prior to curing. The polymerizable dental resins or blends comprising these resins also display a flexural strength greater than or equal to about 15,000, preferably greater than or equal to about 16,000, more preferably greater than or equal to about 17,000, and most preferably greater than or equal to about 18,000 psi (pounds per square inch) upon curing with the Cure-Lite™ curing unit for a time period of about 2 to about 5 minutes.

EXAMPLE 4

A dental composite containing an epoxy/methacrylate resins BAEM1 from Example 1 and an ethoxylated$_6$ bisphenol A dimethacrylate available under the trade designation CD541 from Sartomer in 50/50 wt % ratio was prepared. The resin contains cationic and free radical initiators of 3 wt % diaryliodonium hexafluoro antimonite (SarCat®CD 1012), 0.4% CQ and 0.8% EDMAB. The paste is composed of 26% resin, 2% silane treated OX50 (Degussa Corp.), 52% silane treated barium glass filler with an average particle sizes of 0.7 micrometers (Schott Glass) and 20% zirconium silicate filler. Shrinkage was measured using a mercury dilatometer developed by NIST. The shrinkage of this composite is about 1.5% by volume upon setting. As a comparison, a composite product available under the trade designation SIMILE™ (Pentron Corp.) with a similar filler composition was also tested. The shrinkage of the SIMILE™ composite is about 2.3% by volume.

EXAMPLE 5

A bromine-containing methacrylate/epoxy resin was synthesized from the reaction of HEMA or CLMA with brominated bisphenol A diglycidyl ether (BRDGEBA) using the same method as described in Example 1. The molar ratio of hydroxyl group to epoxy was 0.5. The resulting methacrylate/epoxy resin from HEMA and CLMA are abbreviated as BRBAEM1 and BRBAEM2, respectively.

EXAMPLE 6

Resin combinations of BRBAEM2 and EBPADMA in 50/50 wt % ratio with different initiation systems were prepared and their flexural strengths were compared as shown in Table 4. In Sample 19, both cationic polymerization of epoxy and free radical polymerization of methacrylate were utilized. In Sample 20, only free radical polymerization of methacrylate was utilized.

TABLE 4

| Sample No. | Initiating System | Flexural Strength (psi) |
|---|---|---|
| 19 | 3% CD1012, 0.3% CQ, 0.2% EDMAB | 15934 (791) |
| 20 | 0.3% CQ, 0.2% EDMAB | 15105 (972) |

Table 4 shows no difference between the strength of Sample 19 and Sample 20. The addition of cationic photo initiator does not increase the strength in this case.

EXAMPLE 7

Dental composite (Sample 21) containing an epoxy/methacrylate resin BREPMA2 and an ethoxylated$_6$ bisphenol A dimethacrylate available under the tradename CD541 (Sartomer) in 50/50 wt % ratio was prepared. Shrinkage as well as strength was tested. As a comparison, a paste (Sample 22) containing a commercial resin system (SIMILE™, (Pentron Corp.) having a combination of BisGMA/PCBisGMA/UDMA/HDDMA (each of 25%) was also prepared and tested. In both resin systems, no cationic photoinitiator was added. Both resins contain free radical initiators 0.3% CQ and 0.6% EDMAB. Both Samples 21 and 22 have 35 wt % resin, 10 wt % Aerosil R 7200 (Degussa) and 55 wt % zirconium silicate filler as above. The modulus of rupture (MOR), an indicator of flexural strength, and shrinkage of these two composites are compared in Table 5. Shrinkage was measured using a mercury dilatometer developed by NIST. Results are shown below in Table 5.

TABLE 5

| Sample No. | MOR (psi) | Shrinkage |
|---|---|---|
| 21 | 16023 (1624) | 1.9 |
| 22 | 16197 (1533) | 2.8 |

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended embodiments.

We claim:

1. A polymerizable dental resin composition comprising an oligomer comprising units having the structure:

$$AB \qquad (I)$$

wherein A is an organic radical comprising 1 to about 6 (meth)acrylate groups and 0 to about 5 hydroxy groups; and B is an organic radical comprising 1 to about 5 epoxide groups, wherein A and B are linked through the reaction of an epoxide and a hydroxy group; and
a curing system consisting of a free radical cure initiator and a free radical cure accelerator.

2. The polymerizable dental resin composition of claim 1, wherein the ratio of total epoxide groups to (meth)acrylate groups is about 1:10 to about 10:1.

3. The polymerizable dental resin composition of claim 1, wherein the ratio of total epoxide groups to (meth)acrylate groups is about 1:5 to about 5:1.

4. The polymerizable dental resin composition of claim 1, wherein the ratio of total epoxide groups to (meth)acrylate groups is about 1:2 to about 2:1.

5. The polymerizable dental resin composition of claims 1, wherein the resin has a volume shrinkage of less than about 8% after curing.

6. The polymerizable dental resin composition of claim 1, wherein the resin has a volume shrinkage of less than about 2% after curing.

7. A curable dental restorative material comprising:
the polymerizable dental resin composition of claim 1;
optionally, up to 90 weight % of a filler system based on the total weight of the dental restorative material; and
a curing system consisting of a free radical cure initiator and a free radical cure accelerator.

8. The dental restorative material of claim 7, further comprising about 1 to about 90 weight % filler based on the total weight of the dental restorative material.

9. A method of making a dental restoration, comprising applying to a site to be restored a composition comprising
a curing system consisting of a free radical cure initiator and a free radical cure accelerator; and
an oligomer comprising units having the structure:

$$AB \qquad (I)$$

wherein A is an organic radical comprising 1 to about 6 (meth)acrylate groups and 0 to about 5 hydroxy groups; and B is an organic radical comprising 1 to about 5 epoxide groups, wherein A and B are linked through the reaction of an epoxide and a hydroxy group; and
curing the composition to form a dental restoration.

* * * * *